United States Patent  (10) Patent No.: US 9,309,559 B2
Loudig et al.  (45) Date of Patent: Apr. 12, 2016

(54) SIMULTANEOUS EXTRACTION OF DNA AND RNA FROM FFPE TISSUES

(71) Applicant: ALBERT EINSTEIN COLLEGE OF MEDICINE OF YESHIVA UNIVERSITY, Bronx, NY (US)

(72) Inventors: Olivier Loudig, Briarcliff Manor, NY (US); Adam Kotorashvili, Bronx, NY (US); Thomas Rohan, New York, NY (US)

(73) Assignee: Albert Einstein College of Medicine, Inc., Bronx, NY (US)

(*) Notice: Subject to any disclaimer, the term of this patent is extended or adjusted under 35 U.S.C. 154(b) by 16 days.

(21) Appl. No.: 14/249,631

(22) Filed: Apr. 10, 2014

(65) Prior Publication Data
US 2014/0308670 A1    Oct. 16, 2014

Related U.S. Application Data

(60) Provisional application No. 61/812,117, filed on Apr. 15, 2013.

(51) Int. Cl.
C07H 21/00 (2006.01)
C12Q 1/68 (2006.01)
C12N 15/10 (2006.01)

(52) U.S. Cl.
CPC .......... *C12Q 1/6806* (2013.01); *C12N 15/1003* (2013.01)

(58) Field of Classification Search
CPC .......................... C12Q 1/6806; C12N 15/1003
USPC ............................................. 536/25.4, 25.41
See application file for complete search history.

(56) References Cited

U.S. PATENT DOCUMENTS 8,581,038 B2 * 11/2013 Lagudah et al. ............... 800/279

OTHER PUBLICATIONS

Rubio-Piña et al. Electronic Journal of Biotechnology vol. 11, No. 4, 2008 pp. 1-5.*
Kotorashvili A et al., entitled "Effective DNA/RNA Co-Extraction for Analysis of MicroRNAs, mRNAs, and Genomic DNA from Formalin-Fixed Paraffin-Embedded Specimens," PloS One, Apr. 2012, vol. 7, Issue 4, e34683, pp. 1-11.

* cited by examiner

*Primary Examiner* — Jezia Riley
(74) *Attorney, Agent, or Firm* — Amster, Rothstein & Ebenstein LLP

(57) ABSTRACT

The present provides methods and kits for extracting DNA and RNA from FFPE tissues and samples.

19 Claims, 16 Drawing Sheets

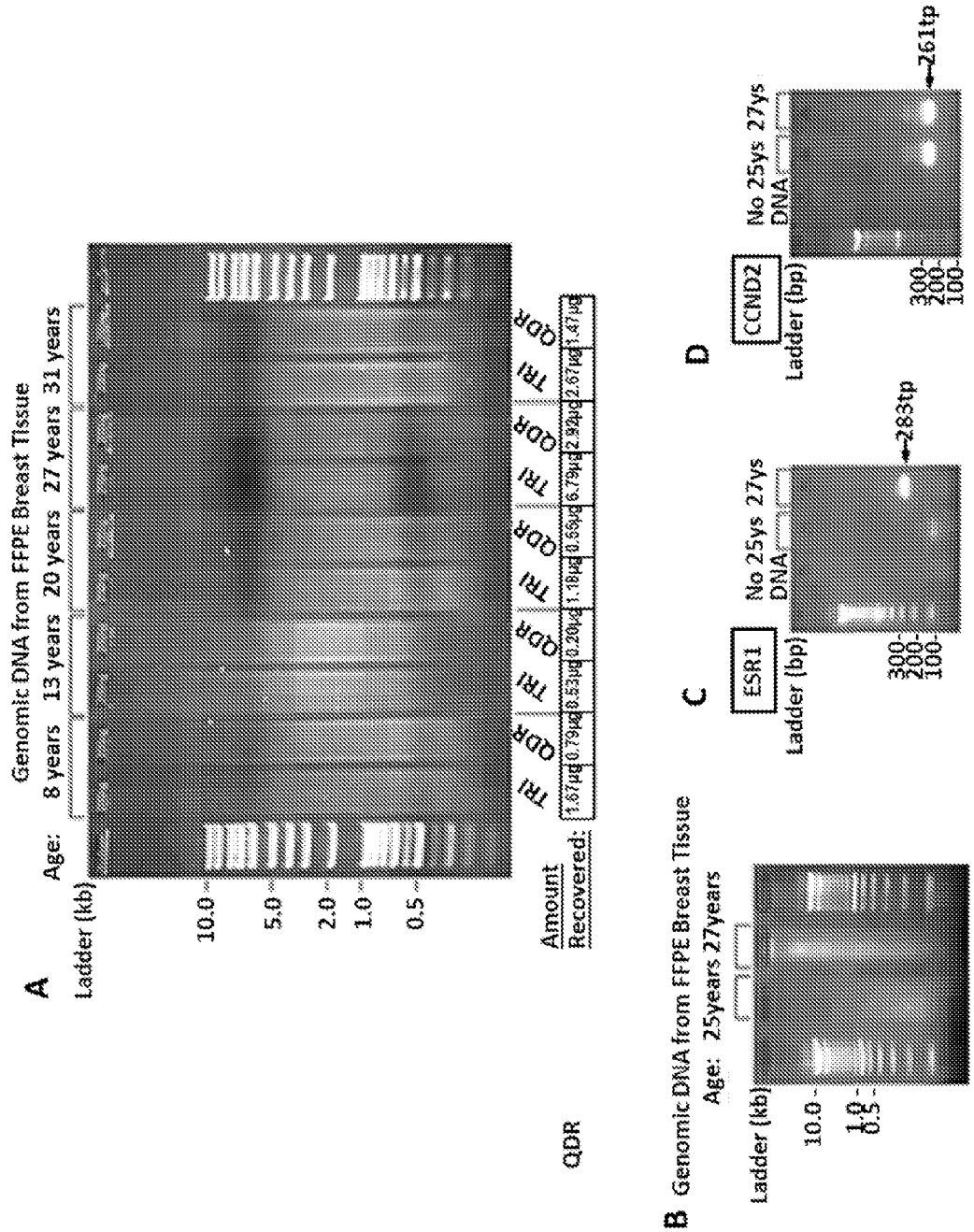
Fig. 9A-D

SIMULTANEOUS EXTRACTION OF DNA AND RNA FROM FFPE TISSUES

CROSS-REFERENCE TO RELATED APPLICATIONS

This application claims benefit of U.S. Provisional Application No. 61/812,117, filed Apr. 15, 2013, the contents of which are hereby incorporated by reference.

BACKGROUND OF THE INVENTION

Throughout this application various publications are referred to in square brackets. Full citations for these references may be found at the end of the specification. The disclosures of these publications, and of all patents, patent application publications and books referred to herein, are hereby incorporated by reference in their entirety into the subject application to more fully describe the art to which the subject invention pertains.

Archived human specimens, with known clinical follow-up, represent a valuable resource, particularly for retrospective molecular studies and identification of biological markers that might be useful for risk prediction of disease or prognosis [1].

Recent studies have demonstrated that nucleic acids recovered from archived specimens are suitable for a variety of downstream genetic (genomic and transcriptomic) and epigenetic analyses [1]. Genomic DNA recovered from archived specimens, while degraded, can be analyzed by polymerase chain reaction (PCR) [2,3], array comparative genomic hybridization (CGH) [4], massively parallel sequencing [5], and methylation assays [6-8].

Contrastingly, messenger RNA molecules recovered from formalin-fixed paraffin-embedded (FFPE) specimens display a large extent of degradation, and thus many studies have aimed at demonstrating their suitability for molecular analyses and specific protocols have been established for quantitative reverse transcription PCR (qRT-PCR) [2,9], high-throughput gene expression [1,10-12], and even massive parallel sequencing [13,14]. Interestingly, microRNAs, due to their small size, remain intact throughout the processes of formalin-fixation and RNA extraction, and they can be reliably studied in FFPE specimens [15,16].

Protocols for genomic DNA or total RNA extractions, from FFPE specimens, have been well documented and made available as reliable commercial kits [17,18]. In general, tissue sections are deparaffinized in a non-polar solvent: xylene, Hemo-D (dlimonene), or citrisolv and then subjected to proteinase-K digestion, usually short (15 minutes to overnight) for RNA, to minimize degradation, but extended (for up to 48 h) for DNA isolation [1]. To increase DNA purity, exposure to high-temperature (95-98° C.), in an alkaline buffer, has been shown to allow removal of DNA/protein cross-links, a denaturing step however that cannot be used during RNA isolation [19-22]. To avoid cross-contamination between these two types of nucleic acids, an RNase or DNAse treatment for DNA or RNA purification, respectively, is added prior to either a solvent separation (TRIzol, phenol/chloroform) or a silica-based column purification [11,18]. To increase RNA quality, a final step consists of heat-treatment at 70° C. for up to 60 minutes, in a Tris-EDTA (1× TE) or citrate-based buffer, to remove chemical modifications (methylol groups) acquired during formalin-fixation [23,24]. Based on these different biochemical requirements, DNA and RNA have routinely been extracted separately.

The recovery of genomic DNA and total RNA from the same specimen would have the advantage of providing matched nucleic acid fractions, from the same cells, which would be extremely valuable for validations as well as for integrative studies. Maximizing DNA and RNA retrieval from a single specimen might also be very useful when using tissues that are of limited availability.

The present invention addresses the need for simultaneously recovering RNA and DNA from the same specimen sample, including FFPE archival samples, fresh samples, sera and serum exosomes.

SUMMARY OF THE INVENTION

The present invention addresses a need for more effective methods of co-extracting nucleic acids from fixed specimens.

A method is provided of recovering both RNA and DNA from a biological sample comprising contacting the sample with a monophasic solution comprising phenol and guanidine isothiocyanate, obtaining RNA from the resultant upper phase, contacting the resultant lower phase with an amount of ethanol and centrifuging for a time sufficient to create a pellet, contacting the pellet with an amount of a first buffer solution and proteinase K, purifying DNA from the pellet by contacting with an amount of a second buffer and an amount of ethanol, binding, washing and eluting the DNA so as to obtain the DNA, thereby recovering both RNA and DNA from the same biological sample.

A kit for performing the method is also provided.

BRIEF DESCRIPTION OF THE DRAWINGS

FIG. 1A shows a schematic representation of DNA recovery from the lower phase of TRIzol (upper phase yields RNA). In step 1 (yellow bullet), tissue digestion is performed following the procedure described in Loudig et al. 2007. In step 2 (yellow bullet), using TRIzol RNA and DNA are separated into the upper and lower phases, respectively. The DNA is recovered from the lower phase, using the optimized approach described in the materials and methods. The four steps describing optimization of DNA recovery from the lower phase of TRIzol include: a. Precipitate DNA; b. Process DNA pellet (using reagents from Qiagen DNA FFPE kit for steps b to d); c. Purify DNA; d. Bind, wash, and elute DNA. FIG. 1B shows the analysis of DNA from FFPE tissue recovered from the lower phase of TRIzol. The upper panel shows the histogram of DNA recovery. The lower panel shows a 1.5% agarose gel electrophoresis image of fresh DNA recovered from a TRIzol treatment lower phase (lane 1), FFPE DNA recovered from a TRIzol lower phase (lanes 2-6), and the size ladder (lane 7). For DNA, precipitation was tested for 600 ml (lane 2 and lane 4), 1000 ml (lane 3 and lane 5), and 1200 ml of Ethanol (lane 6). Proteinase K (PK) treatment was performed for 24 (lanes 2-3) or 48 hours (lanes 4-6). Electrophoresis reveals integrity of the extracted DNA samples. The histogram and agarose gel show that precipitation with a combination of 1200 ml ethanol and 48 hours of PK treatment gives the best quality and quantity of DNA. 500 ng of DNA was loaded per well of the gel.

FIG. 2 shows the results from four different methods of extracting DNA or RNA from archived human specimens. FIG. 2A shows results from the Qiagen QIAamp DNA FFPE kit for DNA (QD). FIG. 2B shows results from the TRIzol DNA/RNA extraction method for DNA and RNA (TRI). FIG. 2C shows results from the Qiagen AllPrep DNA/RNA FFPE kit for DNA and RNA (QDR). FIG. 2D shows results from the Ambion RecoverAll™ Total Nucleic Acid Isolation (AMB) for DNA and for RNA. Each nucleic acid extraction was done in triplicate to determine technical reproducibility.

FIG. 3 is a summary of the results from sequential recovery of DNA and RNA from MCF10A Fresh and FFPE samples using different extraction methods. FIG. 3A shows a schematic representation of cell culture and DNA/RNA extraction methods used with matched fresh and 1 month-old formalin-fixed paraffin-embedded (FFPE) human mammary epithelial MCF10A cells. FFPE DNA and RNA extractions (QD, TRI, QDR, AMB) were performed in triplicate using three 10 mm sections for each replicate. FIG. 3B shows an analysis of RNA extracted from matched fresh and FFPE MCF10A cells. Total RNA extracted from fresh cells using TRIzol (TRI-Fr; Lane 2), and total RNA extracted from FFPE cells using TRIzol (TRI; lane 3), Qiagen QIAamp DNA/RNA extraction kit (QDR; lane 4), and AMBion RecoverAll™ Total Nucleic Acid Isolation kit (AMB; lane 5) was analyzed and quantified using an Agilent 2100 Bioanalyzer 6000 Nanochip (size ladder in lane 1). The bar graph placed above the Bioanalyzer image displays total amounts of RNA recovered from three consecutive 10 mm sections, in triplicate experiments, using the three different methods (TRI, QDR, AMB). FIG. 3C shows an analysis of genomic DNA extracted from matched fresh and FFPE MCF10A cells. DNA was extracted from fresh cells using a phenol/chloroform based method (PC-Fr; lane 2), and TRIzol (TRI-Fr lane 3); and from FFPE cells using Qiagen QIAamp DNA FFPE kit (QD; lane 4), TRIzol DNA/RNA extraction method (TRI; lane 5), Qiagen AllPrep DNA/RNA FFPE kit (QDR; lane 6), and AMBion RecoverAll™ Total Nucleic Acid Isolation kit (AMB; lane 7) was analyzed on a 1% agarose gel (size ladder in lane 1). The bar graph placed above the agarose gel displays total amounts of DNA recovered alone (QD), simultaneously with RNA (TRI, QDR), or separately from RNA (AMB), using three consecutive 10 mm sections, in triplicate experiments for each method.

FIG. 4 shows a microRNA expression analysis of matched fresh and FFPE RNA from MCF10A cells using different RNA extraction methods. The upper panel displays a graphic representation of quantitative RT-PCR (TaqmanH miRNA assays). Measurements obtain for miR-10a, miR-196b, miR-135b, miR-32a and miR-21 using matched fresh and FFPE RNA from MCF10A cells. MiRNAs were quantified using FFPE RNA extracted with TRIzol (TRI), Qiagen AllPrep DNA/RNA FFPE (QDR), AMBion RecoverAll™ Total Nucleic Acid Isolation (AMB) kits and compared to control RNA extracted from fresh cells with TRIzol (TRI-Fr). Results are represented as DdCt (dCt target miRNA-dCt miR-10a (least expressed miRNA)). The lower panels show the comparison of global miRNA quantification obtained between fresh and FFPE RNA samples using the Illumina miRNA platform. Comparisons were performed between triplicate RNA extractions obtained from matched fresh (TRI-Fr1, TRI-Fr2, TRI-Fr3) and FFPE (TRI1-3, QDR1-3, and AMB1-3) cells. The correlation coefficient (r) between matched fresh and FFPE RNAs is displayed in each graph.

FIG. 5 shows a messenger RNA expression analysis of matched fresh and FFPE RNA using different RNA extraction methods. The upper panel displays a graphic representation of quantitative RT-PCR (TaqmanH mRNA assays) Measurements obtained for ESR1, CCND2 and KRT14 genes using matched fresh and FFPE RNA from MCF10A cells. The three genes were quantified using matched fresh RNA recovered with TRIzol (TRI-Fr), and FFPE RNA recovered with TRIzol (TRI), with Qiagen AllPrep DNA/RNA FFPE (QDR), with AMBion RecoverAll™ Total Nucleic Acid Isolation (AMB) and with the Roche RNA FFPE (Roche) kits. The results are represented as fold changes. The lower panels show the comparison of global mRNA quantifications obtained between fresh and FFPE RNA samples using the Illumina whole-Genome DASL platform. The different panels display comparison between triplicate RNA extractions from matched fresh (TRI-Fr1, TRI-Fr2, TRI-Fr3 (bottom to top panel)) and FFPE (TRI1-3, QDR1-3, AMB1-3 and Roche1-3 (from left to right panel)) cells. The correlation coefficient (r) between matched fresh and FFPE RNAs is displayed in each graph.

FIG. 6 shows a methylation analysis of CpG regions in genes of interest using matched fresh and FFPE genomic DNA obtained by different extraction methods. FIG. 6A shows a representative 2% agarose gel electrophoresis images of PCR products for ESR1 genes. FIG. 6B shows a representative 2% agarose gel electrophoresis images of PCR products for CCND2 genes. FIG. 6C is a graph depicting methylation values as a percentage for CpG dinucleotide rich regions in ESR1 as assayed via the MassARRAY system (Sequenom). FIG. 6D is a graph depicting methylation values as a percentage for CpG dinucleotide rich regions in CCDN2 as assayed via the MassARRAY system (Sequenom). FIG. 6E is a graph depicting methylation values as a percentage for CpG dinucleotide rich regions in GHSR as assayed via the MassARRAY system (Sequenom). FIG. 6F is a graph depicting methylation values as a percentage for CpG dinucleotide rich regions in ARID3A as assayed via the MassARRAY system (Sequenom). Data were analyzed and confirmed using the MassArray R script statistical package. Methylation values for fresh MCF10A DNA isolated with control methods (DNA from fresh cells recovered by phenol/chloroform (PC-Fr) and from FFPE cells using the Qiagen QIAamp DNA FFPE kit (QD)) are compared against methods used for matched FFPE DNA (TRIzol extraction (TRI), Qiagen AllPrep DNA/RNA FFPE (QDR), and AMBion RecoverAll™ Total Nucleic Acid Isolation (AMB)). The bar graphs display the correlation between DNA methylation measurements obtained from fresh genomic DNA and each FFPE genomic DNA recovered by the different extraction methods.

FIG. 7 shows results from the co-extraction of total RNA and genomic DNA from fresh mouse tissues using TRIzol. RNA and DNA were extracted from brain, muscle, heart and liver in triplicate to determine technical reproducibility using TRIzol and following manufacturer's instructions. Based on simultaneous extractions of DNA and RNA performed using TRIzol this study consistently recovered more RNA than DNA and recovery of DNA appears highly reproducible.

FIG. 8 shows a comparison of RNA extraction between the Ambion RecoverAll™ kit (AMB) and the TRIzol-based optimized method (TRI) using archived normal and tumor human breast tissues. Total RNA was recovered from normal breast tissue (see left side of graph) and from tumor breast tissue (see right side of graph). For normal tissue (left side of graph), total RNA was extracted from two, three, and four 10 µm sections, in triplicate experiments, using either the AMB or TRI methods. For tumor tissue (left right of graph), total RNA was extracted from one, two, and three 10 µm sections, in triplicate experiments, using either the AMB or TRI methods. The average of total RNA, in micrograms, of three experiments was plotted and error bars were determined for each individual condition.

FIG. 9: FIG. 9 shows results from electrophoretic and methylation analyses of genomic DNA recovered from older formalin-fixed paraffin-embedded benign breast disease tissue specimens. FIG. 9A shows an analysis of 200 ng of genomic DNA recovered from 8, 13, 20, 27 and 31 year-old BBD tissue specimens using the TRIzol-based optimized method (TRI) and the Qiagen AllPrep DNA/RNA FFPE (QDR) kit. For each specimen 5×10 μm sections were used for each method and the total amounts of genomic DNA recovered are displayed below the image of the agarose gel, showing that TRI provides at least twice the amount of DNA than QDR. The genomic DNA displays an overall degraded profile identical in both methods. FIG. 9B shows a 1% agarose gel analysis of 25 (low quality DNA) and 27 (medium quality DNA) year-old breast specimens displaying significant differences in genomic DNA quality. FIG. 9C shows a methylation analysis of CpG regions of ESR1 (283 bp region) using FFPE genomic DNA from the 25- and 27-year-old BBD tissue specimens and representative images of the PCR products on a 2% agarose gel. FIG. 9D shows a methylation analysis of CpG regions of CCND2 (261 bp region) using FFPE genomic DNA from the 25- and 27-year-old BBD tissue specimens and representative images of the PCR products on a 2% agarose gel. Lower quality genomic DNA (25 year old specimen) did not yield a PCR product indicating either absence of methylation or failed PCR reaction, possibly due to low genomic DNA quality.

DETAILED DESCRIPTION OF THE INVENTION

Figure 1A:
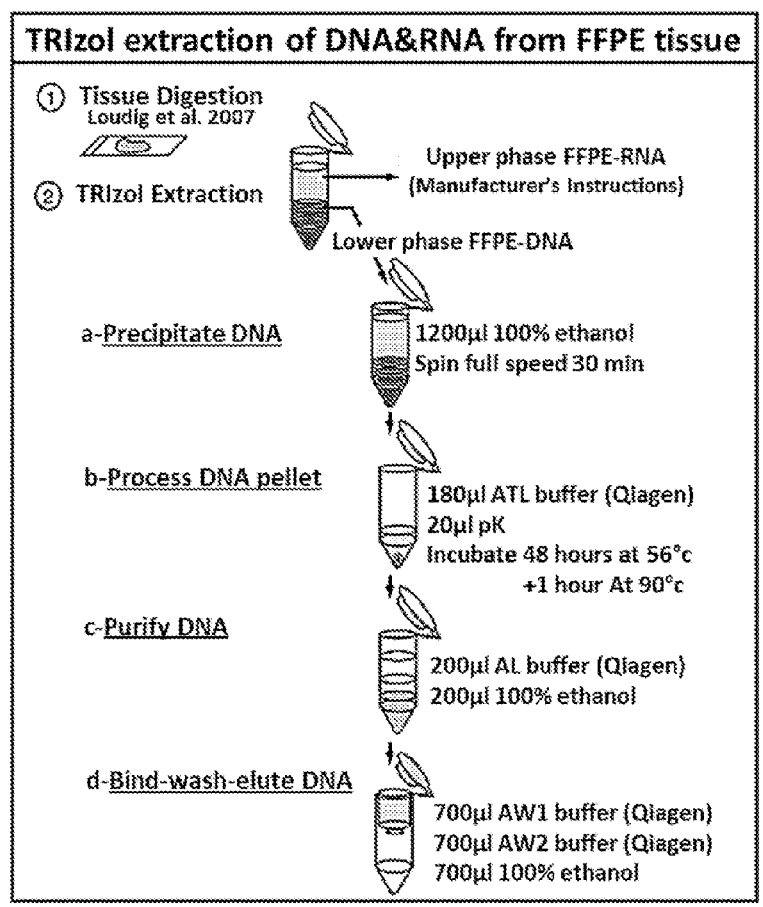
FIGS. 1A-1B.

A method is provided of recovering both RNA and DNA from a biological sample comprising
contacting the sample with a monophasic solution comprising phenol and guanidine isothiocyanate,
obtaining RNA from the resultant upper phase,
contacting the resultant lower phase with an amount of ethanol and centrifuging for a time sufficient to create a pellet,
contacting the pellet with an amount of a first buffer solution and proteinase K,
purifying DNA from the pellet by contacting with an amount of a second buffer and an amount of ethanol,
binding, washing and eluting the DNA so as to obtain the DNA,
thereby recovering both RNA and DNA from the same biological sample.

In an embodiment, the biological sample is a single sample. In an embodiment, the biological sample is an archived sample. In an embodiment, the biological sample is a fresh sample.

A kit for performing the method is also provided, wherein the kit comprises reagents recited herein necessary to effect the method.

In an embodiment, the monophasic solution is TRIzol® (Life Technologies, CA) or is an equivalent solution.

RNA precipitation: In an embodiment, RNA is obtained from the upper phase by a method comprising the following:
1. (Optional) When precipitating RNA from small sample quantities (<$10^6$ cells or <10 mg tissue), add 5-10 μg of RNase-free glycogen as a carrier to the aqueous phase.
Note: Glycogen is co-precipitated with the RNA, but does not inhibit first-strand synthesis at concentrations ≤4 mg/mL, and does not inhibit PCR.
2. Add 0.5 mL of 100% isopropanol to the aqueous phase, per 1 mL of TRIzol® Reagent used for homogenization.
3. Incubate at room temperature for 10 minutes.
4. Centrifuge at 12,000×g for 10 minutes at 4° C.

Note: The RNA is often invisible prior to centrifugation, and forms a gel-like pellet on the side and bottom of the tube.
5. Proceed to RNA wash.
RNA Wash
1. Remove the supernatant from the tube, leaving only the RNA pellet.
2. Wash the pellet, with 1 mL of 75% ethanol per 1 mL of TRIzol® Reagent used in the initial homogenization.
Note: The RNA can be stored in 75% ethanol at least 1 year at −20° C., or at least 1 week at 4° C.
3. Vortex the sample briefly, then centrifuge the tube at 7500×g for 5 minutes at 4° C. Discard the wash.
4. Vacuum or air dry the RNA pellet for 5-10 minutes. Do not dry the pellet by vacuum centrifuge.
Note: Do not allow the RNA to dry completely, because the pellet can lose solubility. Partially dissolved RNA samples have an A260/280 ratio <1.6.
5. Proceed to RNA resuspension.

In an embodiment, phase separation is achieved as follows:
1. Incubate the homogenized sample (see Homogenizing samples) for 5 minutes at room temperature to permit complete dissociation of the nucleoprotein complex.
2. Add 0.2 mL of chloroform per 1 mL of TRIzol® Reagent, or equivalent, used for homogenization. Cap the tube securely.
3. Shake tube vigorously by hand for 15 seconds.
4. Incubate for 2-3 minutes at room temperature.
5. Centrifuge the sample at 12,000×g for 15 minutes at 4° C.
Note: The mixture separates into a lower red phenol-chloroform phase, an interphase, and a colorless upper aqueous phase. RNA remains exclusively in the aqueous phase. The upper aqueous phase is ~50% of the total volume.
6. Remove the aqueous phase of the sample by angling the tube at 45° and pipetting the solution out. Avoid drawing any of the interphase or organic layer into the pipette when removing the aqueous phase.
7. Place the aqueous phase into a new tube and proceed to the RNA Isolation Procedure.
8. Save the interphase and organic phenol-chloroform phase if isolation of DNA or protein is desired. See DNA Isolation Procedure and Protein Isolation Procedure for details. The organic phase can be stored at 4° C. overnight.

In an embodiment, a further 30-60 minute proteinase K digest is performed, preferable for 45 minutes.

In an embodiment, the monophasic solution also comprises ammonium thiocyanate. In an embodiment, the phenol is 30-60% of the monophasic solution and the guanidine isothiocyanate is 15-40% of the monophasic solution. In an embodiment, the monophasic solution comprises ammonium thiocyanate at 7-13% of the solution.

In an embodiment, the sample comprises a formalin fixed and paraffin embedded biological sample.

In an embodiment, the sample size prior to contacting with the monophasic solution is 100 μL. In an embodiment, the sample is contacted with 1000 μL monophasic solution. In an embodiment, the ethanol added to the lower phase comprises 1000-1200 μL 100% ethanol.

In an embodiment, the first buffer solution is a tissue lysis buffer. In an embodiment, the second buffer solution is nucleic acid isolation buffer comprising a chaotropic salt. In an embodiment, the binding, washing and eluting the DNA comprise contacting with one or more of a first wash buffer, a second wash buffer and ethanol. In an embodiment, the ethanol is 100% ethanol.

In an embodiment, obtaining RNA from the resultant upper phase comprises contacting the upper phase with isopropanol, sodium acetate and linear acrylamide then centrifuging with ethanol a sufficient amount of times to obtain a pellet, air drying the pellet, contacting with buffer and centrifuging a further time so as to obtain the RNA. In an embodiment, the upper phase is separated from the lower phase prior to obtaining the RNA.

In an embodiment, obtaining DNA from the resultant lower phase comprises contacting the lower phase with approximately an equal volume of ethanol. In an embodiment, the lower phase is separated from the upper phase prior to obtaining the RNA.

In an embodiment, the first buffer is about 180 μL of proteinase K digesting buffer and about 20 μL of proteinase K is used.

In an embodiment, the biological sample is formalin-fixed. In an embodiment, the biological sample is paraffin embedded. In an embodiment, the biological sample is deparaffinized prior to being contacted with the monophasic solution. In an embodiment, the biological sample is hydrated and digested prior to being contacted with the monophasic solution, but after being deparaffinized. In a further embodiment, the digestion is effected with a proteinase K.

In an embodiment, the biological sample comprises serum, plasma, blood, urine, tears, saliva, or semen.

In an embodiment, the biological sample comprises a purified exosome. In an embodiment, the exosome is purified from a sample via ultracentrifugation; by precipitation and centrifugation; by magnetic immuno-purification; or by column purification. Exosomes are 60-150 nm membrane vesicles secreted by most cell types in vivo and in vitro. Exosomes are found, for example, in blood, urine, amniotic fluid, malignant ascite fluids and contain distinct subsets of microRNAs depending upon, for example, the tumor from which they are secreted. In an embodiment, the exosomes are from a tumor. Exosomes purified by precipitation and centrifugation can be purified by employing polyethylene glycol (PEG) based reagents, for example Exoquick™ (System Biosciences). Exosome purification by magnetic immuno-purification can be effected by employing one or more antibodies against markers known to be expressed on exosome cell-surfaces, such as CD63, CD44, EpCam, CD67. Exosome purification by column purification can be effected, for example, using ExoRNeasy® (Qiagen). For ultracentrifugation, precipitation with PEG reagents, and magnetic immuno-purification an agent such as TRIZol® is added directly to purified exosome pellets and the procedure followed as described herein. The upper phase will provide the RNA component. The lower phase is processed with Proteinase K, for 48 h for example, as described herein. The DNA is bound to a purification column, washed and eluted. A non-limiting example of a purification column is a Qiagen® DNA purification column. For example, a DNA purification column which comprises a silica membrane assembly for binding of DNA in high-salt buffer and elution with low-salt buffer or water, so as to tremove primers, nucleotides, enzymes, mineral oil, salts, agarose, ethidium bromide, and other impurities from DNA samples. For column purification (e.g., ExoRNeasy® (Qiagen)), Qiazol (an equivalent chemical of TRIZol®, containing 25-50% phenol and 10-25% guanidine thiocyanate) is added to the column. The same steps, as the ones described for TRIZol® herein are followed to recover RNA and DNA separately.

In an embodiment, once exosomes are purified out of a biofluid such as serum, plasma, urine, saliva, tears, or another biofluid, the remaining supernatant can be subjected to the methods claimed herein for obtaining RNA and DNA from a biological sample. Thus in an embodiment, the biological sample comprises a supernatant of exosome purification of a biofluid. This embodiment is particularly important for recovering tumor circulating DNA, viral circulating DNA or other DNAs released into the body's biofluids.

In an embodiment of the methods, the method extracts RNA types other than microRNA and in addition to microRNA.

In an embodiment, the methods further comprise after contacting the resultant lower phase with an amount of ethanol and centrifuging at a temperature below 10° C. for a time sufficient to create a pellet, air drying the pellet and centrifuging it again in an amount of 80% ethanol and then air-drying the pellet, prior to contacting the pellet with an amount of a first buffer solution and proteinase K.

In an embodiment, the pellet is contacted with the first buffer solution and proteinase K for at least a 20 hour period, and then washed and contacted with a second amount of a first buffer solution and proteinase K for at least a second 20 hour period.

In an embodiment, the pellet is contacted with the first buffer solution and proteinase K for at least a 24 hour period, and then washed and contacted with a second amount of a first buffer solution and proteinase K for at least a second 24 hour period.

In an embodiment, incubation with the buffer solution and proteinase K is performed for a time sufficient to digest the majority of cross-linked protein bonds. In an embodiment, incubation with the buffer solution and proteinase K is performed at or around 50-60° C. In an embodiment, incubation with the buffer solution and proteinase K is performed at 56° C.

In an embodiment, the sample comprises genomic DNA.

In an embodiment, the sample comprises microRNA.

In an embodiment, the methods further comprise digesting the biological sample prior to contacting it with the monophasic solution.

In an embodiment, the contacting the pellet with an amount of a first buffer solution and proteinase K is performed for a time sufficient to effect for digestion of the majority of cross-linked proteins.

In an embodiment, in contacting the resultant lower phase with an amount of ethanol, the centrifuging occurs at a temperature below 10° C. for a time sufficient to create a pellet.

In an embodiment of the kit, the kit comprises
an amount of powdered Proteinase K
an amount of a chaotropic reagent for separation of RNA and DNA fractions
one or more binding columns to recover the DNA
optionally, if the RNA is not to be precipitated, a binding column to recover the RNA
optionally, if the RNA is to be precipitated, an amount of linear acrylamide for performing precipitation of RNA
one or more binding buffers for the binding columns
one or more wash buffers for the binding columns
RNAse/DNase-free water for elution of DNA from binding columns.

In an embodiment, the chaotropic agent is a monophasic solution comprising phenol and guanidine isothiocyanate. In an embodiment, the chaotropic agent further comprises ammonium thiocyanate. Examples of chaotropic agents suitable for use in the invention include TRIzol® reagent or QIAzol® reagent, or an equivalent.

In an embodiment, the kit further comprises siliconized RNase/DNase-free eppendorf tubes to prevent nucleic acid adsorption onto tube inner surface.

In an embodiment, the kit further comprises the powdered Proteinase K pre-aliquoted in tubes for resuspension.

In an embodiment, the kit does not comprise a binding column to recover the RNA.

In an embodiment, the kit does comprise a binding column to recover the RNA.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

This study sought to determine if genomic DNA and total RNA could be effectively co-extracted from archived specimens within a single reaction. This study optimized a co-extraction method using TRIzol®, which is the most trusted reagent for total RNA extraction from fresh tissues, because it allows DNA/RNA phase separation and recovery from fresh tissues [25]. Then, using a series of seven human archived specimens, the tested approach was quantitatively compared to two commercial kits designed for either simultaneous (Qiagen AllPrep DNA/RNA FFPE kit) or separate (Ambion RecoverAll™ Total Nucleic Acid Isolation kit) DNA or RNA extractions [26]. Finally, using material recovered from matched fresh and one month-old FFPE MCF10A cells, the study assessed the quality of mRNA by quantitative RT-PCR and global gene expression using the whole-genome cDNA-mediated Annealing, Selection, Extension and Ligation (WG-DASL) assay from Illumina, microRNAs by qRT-PCR and expression profiling, and genomic DNA by methylation assays.

Materials and Methods

Specimens: Formalin-fixed paraffin-embedded (FFPE) specimens were obtained from Dr. Susan Fineberg at the Montefiore Medical Center (MMC), Bronx, N.Y. In accordance with OHRP Guidance on research involving coded private information or biological specimens, this study did not meet the definition of human subject research as defined by 45 C.F.R. §46.102(f), as data/specimens were not collected specifically for the proposed research project and the data/specimens received by Dr. Loudig did not contain a code derived from individual personal information. Thus, experiments using these tissue blocks did not require further monitoring from the Albert Einstein College of Medicine Institutional Review Board (IRB), which also oversees MMC. Electrophoretic analysis and methylation analyses of genomic DNA from older FFPE benign breast tissue samples (8, 13, 20, 25, 27 and 31 year-old) were performed with specimens obtained from Kaiser Permanente Northwest, after approval of a pilot study entitled "Gene Methylation and Oxidative Stress in the Etiology of breast Cancer" from the ethical board, which was supervised by Dr. Thomas Rohan. IRB approval for this study was obtained from the Albert Einstein College of Medicine Institutional Review Board and from the Kaiser Permanente Northwest Institutional Review Board (Portland), which waived the requirement to obtain informed consent prior to use of these specimens. The tissue blocks were cut on a standard microtome (Leica-microsystems) to generate successive 10 μm sections. Fresh mouse tissues were recovered from dead animals after they had been sacrificed and analyzed in the laboratory of Dr. Rachel Hazan at the Albert Einstein College of Medicine. The animal use protocol was reviewed and approved by the Animal Institute Committee (AIC) of Albert Einstein College of Medicine, the institution's animal care and use committee, on Nov. 6, 2008. AIC approved the protocol for a period of 3 years from the approval date. The approved Animal Welfare Assurance (A3312-01) is on file with the Office for Laboratory Animal Welfare. Albert Einstein College of Medicine has been fully accredited by the Association for the Assessment and Accreditation of Laboratory Animal Care (AAALAC) since Feb. 22, 1983. This protocol was renewed for a period of 3 additional years on Nov. 6, 2011. The tissues were processed with TRIzol in the laboratory of Dr. Rachel Hazan.

Methods for RNA and DNA Extraction from Fresh Tissues and Cells: Genomic DNA from fresh tissue (mouse) and cells (human MCF10A) was extracted using phenol/Chloroform method or TRIzol®, following manufacturer's instructions (Invitrogen, CA, USA).

Method for Co-Extraction of RNA and DNA from FFPE Tissue: Using the TRIzol-based method described in Loudig et al. 2007, total FFPE-RNA was obtained from the upper aqueous phase of TRIzol®, and genomic FFPE-DNA from the lower organic phase of TRIzol® [11]. FFPE-DNA was precipitated by addition of 1200 μl of ethanol and 20 μl of sodium acetate (NaAc), incubation at room temperature for 3 minutes, and centrifugation at 16,000 RPM for 30 min at 4° C. The DNA pellet was washed with 100% ethanol, air-dried 50° C., re-suspended in 180 μl ATL buffer from the DNA FFPE kit (Qiagen, CA, USA), and subjected to proteinase K (pK) digestion for 48 hours at 56° C. (20 μl of pK (30 mg/ml) at start and at 24 h). After 48 h, the solution was incubated at 90° C. for 1 h, 200 μl of AL buffer (Qiagen DNA FFPE kit) and 200 μl of 100% ethanol were added to the solution, which was vortexed and transferred to a MinElute column. The column was spun at 8,000 RPM for 1 min and washed with 500 μl AW1 and AW2 buffers, successively. The column was dried by centrifugation at 14,000 RPM for 3 minutes and the DNA was eluted by addition of 20 μl of 1× TE buffer and centrifugation. The DNA was quantified on a NanoDrop ND-1000 spectrophotometer and analyzed on 1% agarose gel prior to methylation assays.

Commercial Kits for Extraction of RNA and DNA from FFPE Tissue: For extraction of FFPE-DNA alone, this study used the QIAamp DNA FFPE kit (Qiagen, CA, USA) following manufacturer's instructions, using 24 hours proteinase K (pK) digestion. For co-extraction of FFPE-DNA and -RNA this study used the Qiagen AllPrep DNA/RNA FFPE kit following manufacturer's instructions. This study used the RecoverAll™ Total Nucleic Acid Isolation kit (Ambion, TX, USA) to extract FFPE-DNA or FFPE-RNA, and following manufacturers' instructions the pK digested FFPE tissue solution was separated into two halves, with one half subjected to DNase for FFPE-RNA purification, and the other half left at 55° C. for 16 hours before RNase treatment and DNA purification. FFPERNA alone was extracted with the High-Pure RNA Paraffin kit (Roche, IN, USA) for analysis on the Whole-Genome cDNAmediated Annealing, Selection, Extension and Ligation (DASL) assay.

Tissue Culture: Non-tumorigenic breast epithelial MCF10A cells were obtained from Dr. Paraic Kenny at the Albert Einstein College of Medicine and they were cultured in DMEM/F12 (Cellgro, VA, USA), supplemented with 5% horse serum (Invitrogen, CA, USA), hydrocortisone (0.5 μg/ml), mouse epidermal growth factor (EGF; 20 ng/ml), insulin (10 μg/ml), cholera toxin (100 ng/ml, Sigma, MO, USA) at 37° C. in a humidified incubator (5% CO2). Fresh and FFPE cells were prepared as described in Loudig et al. 2011 [26].

MicroRNA Expression Profiling: Total RNA (200 ng) from fresh and FFPE cells was subjected to high-throughput miRNA profiling (1,146 miRNAs) using the Illumina miRNA platform (Illumina, CA, USA) on 12 beadchip arrays, according to manufacturer's instructions, as described in Giricz et al.

2011 [16]. Arrays were scanned on a beadarray reader and raw data were obtained using GenomeStudio.

Messenger RNA Expression Profiling: mRNA expression profiling (24,526 features) was performed with total RNA extracted from fresh and FFPE cells (200 ng) using the Illumina Whole genome cDNA-mediated Annealing, Selection, Extension and Ligation (DASL) assay on 32 beadchip arrays, following manufacturer's instructions and according to Loudig et al. 2011 [26]. Beadchip arrays were scanned on a Beadarray Reader (Illumina, CA, USA) and raw data were obtained using GenomeStudio.

MicroRNA and Messenger RNA Quantitative RT-PCR Experiments: MicroRNAs miR-10a, miR-196b, miR-135b, miR-32a and miR-21 were quantified from total RNA from fresh and FFPE cells using Taqman™ miRNA qRT-PCR (Applied Biosystems, CA, USA) as described in Giricz et al 2011. RNU44 and RNU6B were used as endogenous controls for data normalization as described in Giricz et al. 2011 [16]. mRNAs for ESR1, CCND2 and KRT14 were quantified in matched fresh and FFPE RNA using Taqman® gene expression qRT-PCR reagents (Applied Biosystems, CA, USA). Two sets of Taqman® primers for GAPDH were used as endogenous controls for data normalization. Fold-change differences between fresh and FFPE RNA were calculated as described in Loudig et al. 2011 [27].

DNA Methylation Analysis: Methylation was assayed using the procedure described by Thompson et al. 2009 [28]. Sodium bisulfite treatment was performed with 100-200 ng of fresh and FFPE-DNA using the EZ DNA methylation direct kit (Zymo Research, CA, USA), following manufacturers' protocol. PCR primers were designed using Methprimer for methylation PCRs [29], verified in-silico using Bisearch [30] and R MasArray statistical package [28], and the UCSC genome browser [31]. PCR amplification was conducted using FastStart High Fidelity DNA polymerase (Roche, IN, USA), for 42 cycles. DNA methylation analysis was performed on PCR products using the MassArray EpiTYPER system (Invitrogen, CA, USA), which uses base-specific cleavage followed by MALDI-TOF mass spectrometry. Each experiment was performed in triplicate and analyzed on the MassArray Statistical package for the R environment [28].

Statistical Analysis: For FFPE-RNA recovered by four different methods, TRI, QDR, AMB, and Roche, gene expression profiles were measured by WG-DASL assay. Raw expression intensities of mRNAs were normalized by quantile normalization method implemented in GenomeStudio [32]. For each of the four methods, the normalized intensities of three replicates were averaged, and the Pearson rank correlation coefficients between averaged FFPE and each of the three fresh samples were computed. The MicroRNA expression profiles were analyzed and compared in the same fashion between three methods (TRI, QDR, AMB), by computing Pearson correlation coefficient between FFPE and fresh MCF10A cells.

Results

Figure 1B:
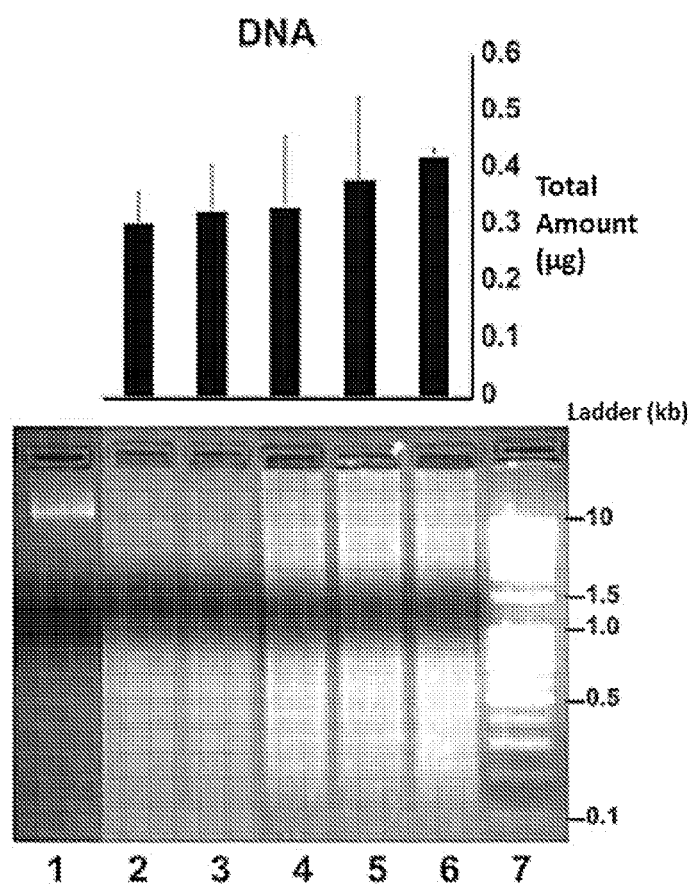
Figure 7:
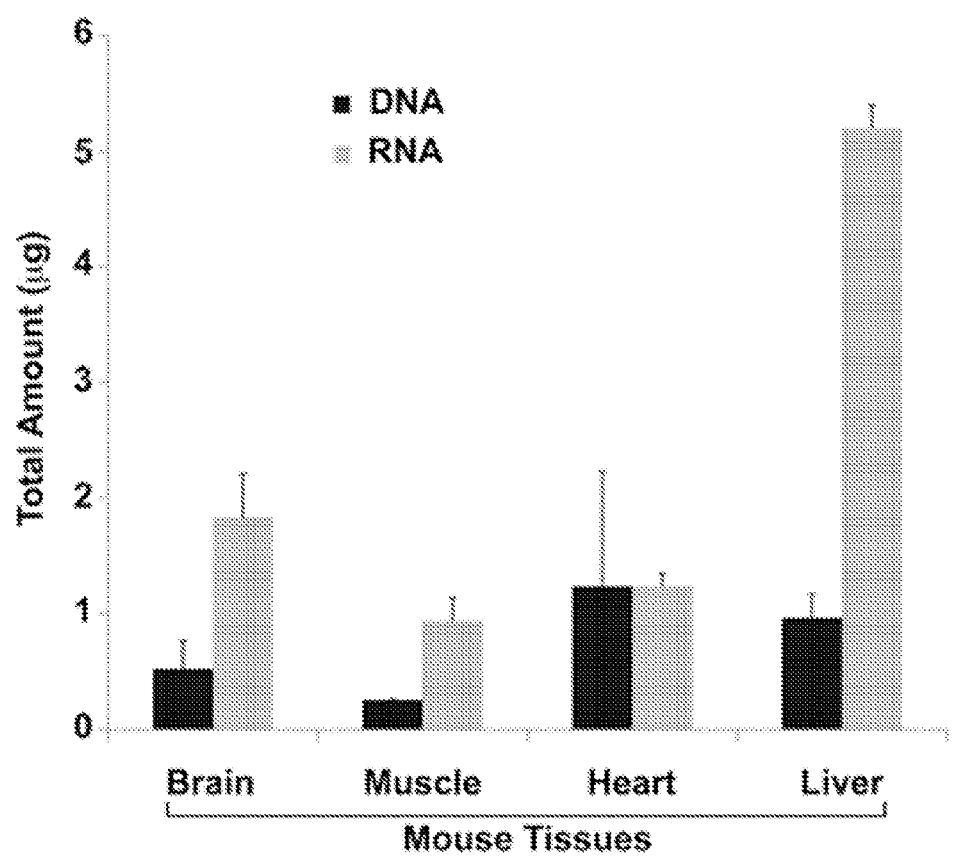
FIG. 7.

FFPE-DNA Extraction from the Lower Phase of TRIzol®: For fresh tissue, DNA and RNA can be simultaneously but separately extracted from the lower organic and the upper aqueous phase of TRIzol®, respectively (FIG. 7; see DNA/RNA from fresh mouse brain, muscle, heart and liver tissues). Considering that the optimized RNA extraction method for FFPE tissues [12] uses TRIzol® as the final chaotropic reagent, this study sought to determine if FFPE-DNA could be precipitated from the lower aqueous phase of TRIzol®. While an FFPE-DNA pellet was observable and DNA readable on a NanoDrop ND-1000, it could not be observed on an agarose gel and did not produce PCR amplicons (data not shown). It was hypothesized that 45 minutes of proteinase-K (pK) treatment, designed for optimal FFPE-RNA recovery, was insufficient for removing FFPE-DNA/protein cross-linkages and thus this study subjected the DNA pellet to additional pK treatment and purified the FFPE-DNA using the Qiagen QIAamp DNA FFPE kit (FIG. 1A). This approach provided consistent yields with observable FFPE-DNA (FIG. 1B).

Figures 2A, 2B, 2C, 2D:
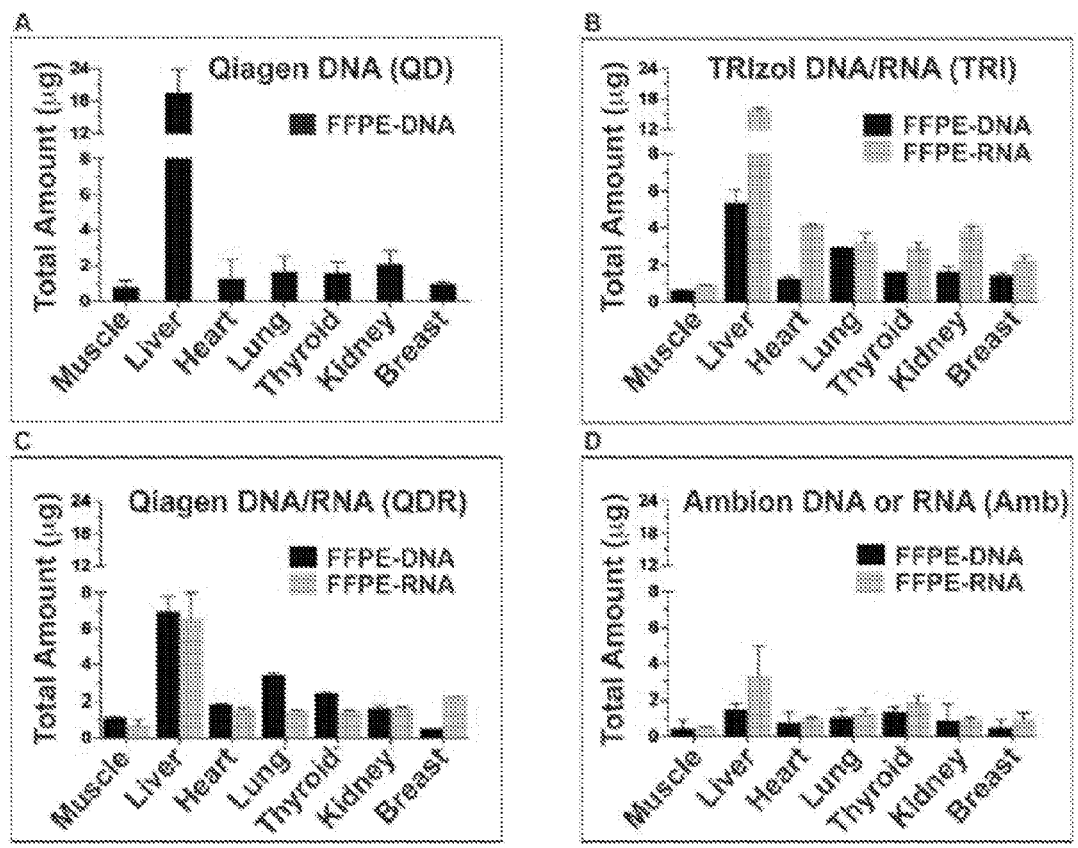
FIGS. 2A-2D.
Figure 3A:
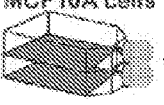
FIGS. 3A-3C.
Figure 3B:
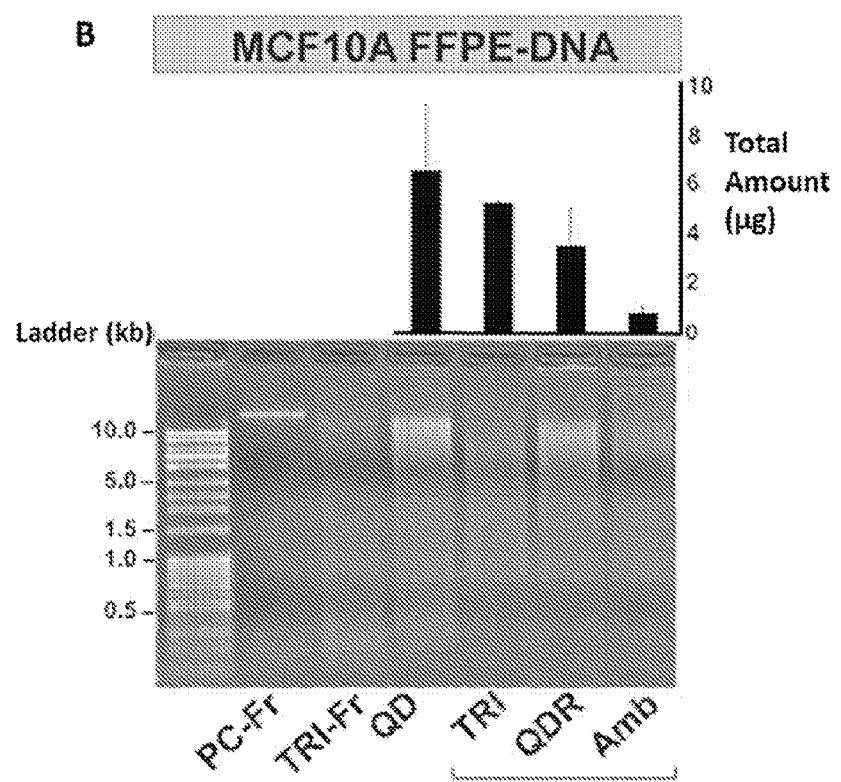
Figure 3C:
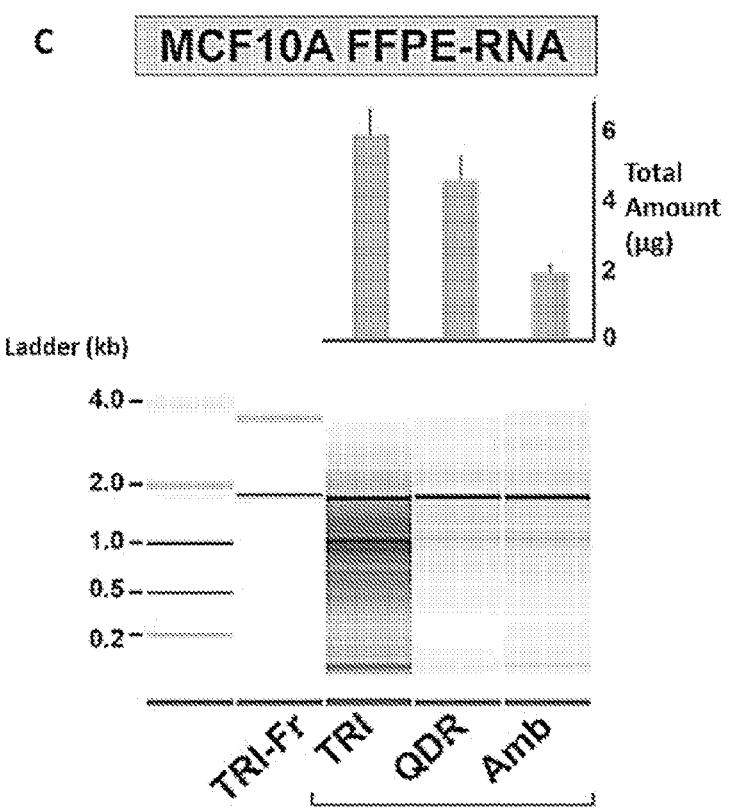
Figure 8:
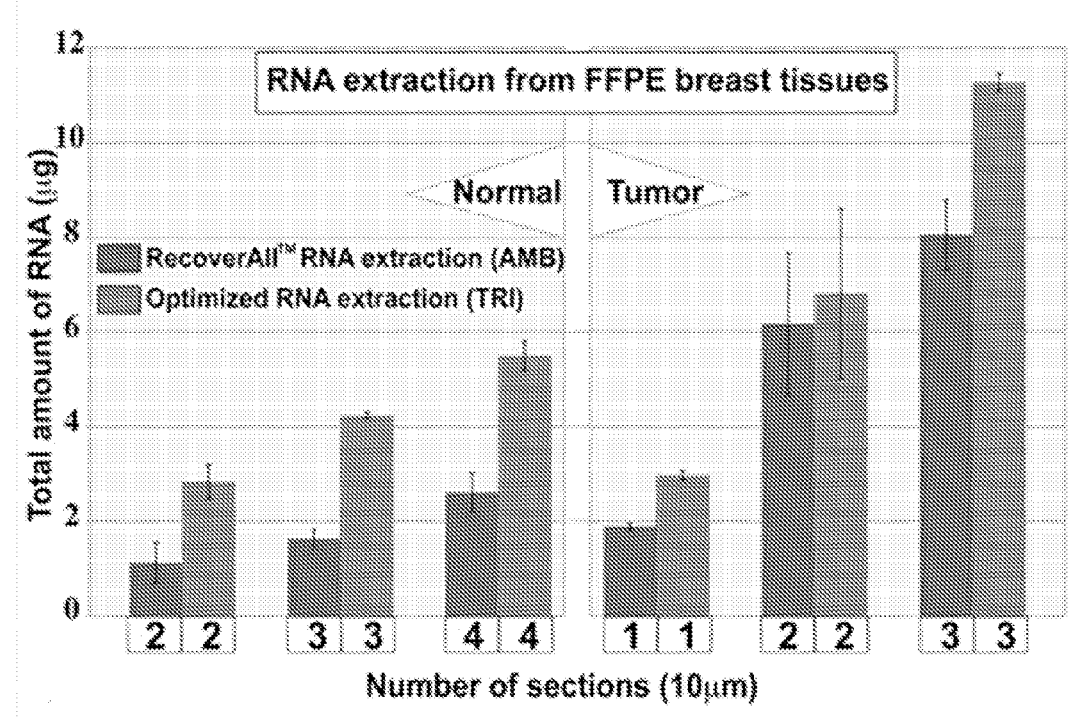
FIG. 8.

DNA and RNA Extraction from Archived Specimens: This study then sought to compare efficiency of the TRIzol®-based FFPE DNA/RNA co-extraction method (TRI; FIG. 2B) to that of two types of commercially available methods, the Qiagen AllPrep DNA/RNA FFPE kit (QDR; FIG. 2C), for co-extraction of DNA and RNA, and the Ambion Recover-All™ Total Nucleic Acid Isolation kit (AMB; FIG. 2D), for separate recovery of DNA and RNA, performed by splitting the pk-digested FFPE tissue. This study used the Qiagen QIAamp DNA FFPE kit as a control for sole recovery of FFPE-DNA (FIG. 2A, QD) and tested the four different extractions with seven different archived tissues (FIG. 2, muscle, liver, heart, lung, thyroid, kidney, and breast). It was observed that sole recovery of FFPE-DNA (FIG. 2A) only provided higher yields than the two co-extraction methods (TRI, QDR) for the liver tissue, but systematically higher yields than AMB. The QDR showed slightly higher FFPE-DNA recovery than the optimized method (TRI) for all tissues but breast (FIGS. 2B and 2C). As expected, both co-extraction approaches provided much higher FFPE-DNA yields than AMB (compare FIGS. 2B and 2C to 2D). For FFPE RNA recovery, the optimized approach (TRI) systematically provided much higher yields than QDR and AMB (FIGS. 2B and 2C). Considering that this study split the pK-digested tissue in two tubes for AMB, to allow recovery of FFPE-DNA and FFPE-RNA, this study also compared the optimized method (TRI) and AMB for extraction of FFPE-RNA alone (FFPE-DNA could still be recovered with the optimized method as it is obtained from the lower aqueous phase of TRIzol®) and determined that the optimized approach still consistently provided higher RNA yields (FIG. 8.). Then, using matched fresh and one-month old FFPE MCF10A cells (FIG. 3A) this study explored the efficiency and reproducibility of the different methods. In this controlled experiment, it was noted that the extraction of FFPE-DNA alone, using QD, yielded the highest amounts of genomic DNA from FFPE cells (FIG. 3B). For these experiments, TRI provided both the highest FFPE-DNA and FFPE-RNA yields when compared to the QDR and AMB methods (FIGS. 3B and 3C). This study then analyzed and compared the quality of the genomic DNA recovered from matched fresh and FFPE MCF10A cells on an agarose gel (FIG. 3B, gel). To obtain the highest DNA quality from fresh cells, this study used a phenol-chloroform (PC-Fr) approach, and observed that DNA recovered from fresh cells, using TRIzol®, displayed a mild profile of degradation (FIG. 3B, gel). For genomic DNA recovered from FFPE cells, QD and QDR appeared to provide higher molecular weight products than TRI and AMB (FIG. 3B, gel). These experiments demonstrate that medium to high quality genomic DNA was recovered from the 1 month-old FFPE MCF10A specimen. Generally, older archived specimens yield lower quality genomic DNA (FIG. 9). When comparing the performance of the two co-extraction methods (TRI and QDR), when using older archived specimens, the optimized approach provided on average twice the amount of genomic DNA obtained with QDR (FIG. 9). This study also analyzed the RNA obtained from matched fresh and 1 month-old FFPE cells, on an Agilent Bioanalyzer, and observed that TRI, QDR and AMB provided similar medium to low quality material with observable 18S ribosomal RNA (FIG. 3C, gel).

Figure 4:
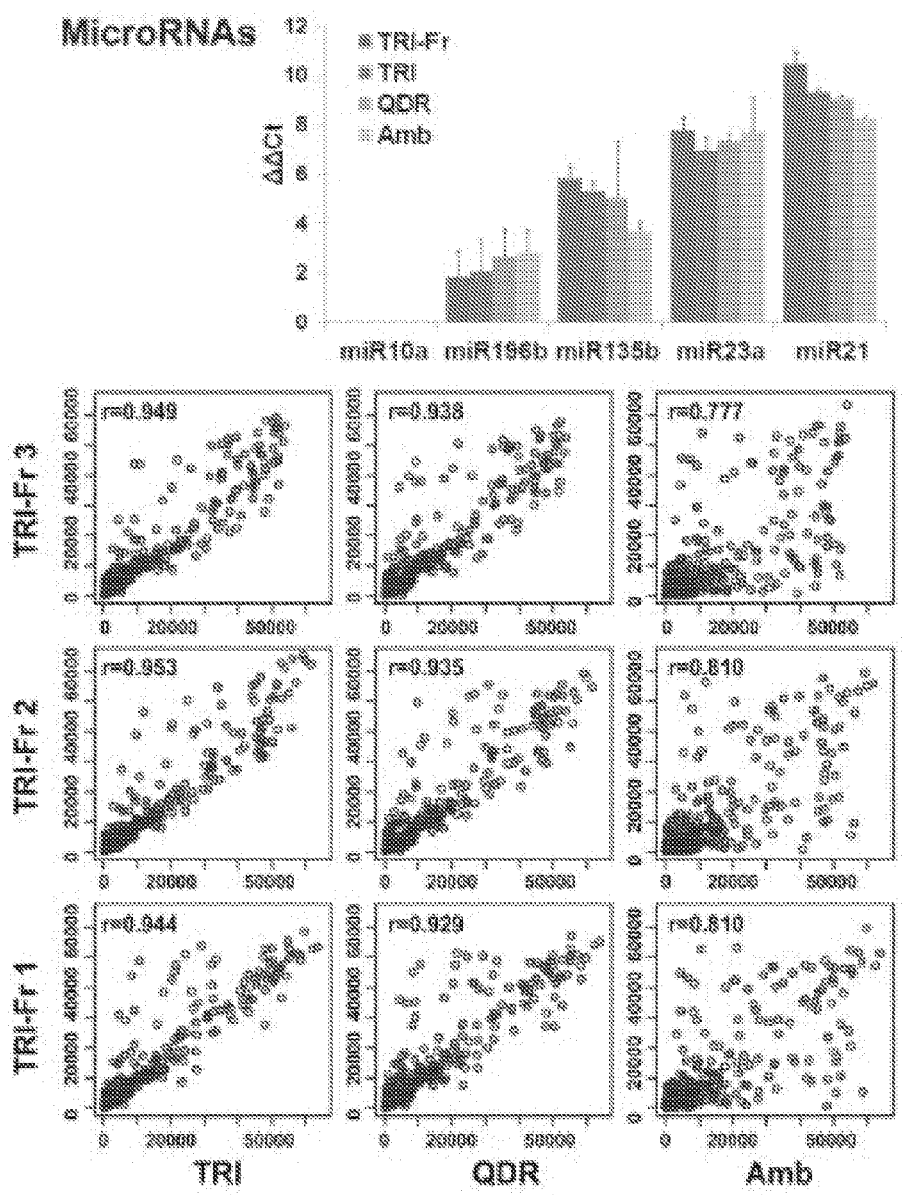
FIG. 4.

Micro-RNA Expression Profiling of Matched Fresh and FFPE RNA: Firstly, this study sought to determine if the different FFPE-DNA/RNA extraction methods might influence miRNA expression measures. Using five miRNAs with known differential expression (from low to high) in fresh MCF10A cells (FIG. 4 bar graph, see TRI-Fr), this study performed qRT-PCR with FFPE-RNA recovered by TRI, QDR, and AMB (FIG. 4 bar graph). QRT-PCR data for miR-135b and miR-21 showed significant decreases, and for miR-196b a significant increase in expression for FFPE-RNA recovered by QDR and AMB, compared to the expression levels of miRNAs recovered from fresh cells (FIG. 4, bar graph TRI-Fr). This study then sought to determine if the extraction method might influence global expression profiling and used the Illumina miRNA expression profiling platform to compare expression of 1,146 miRNAs between matched fresh and FFPE-RNA recovered by TRI, QDR, AMB, each in triplicate measures (FIG. 4, microarray data panels). The results indicate that miRNAs measured in FFPE-RNA recovered by TRI have the highest correlation with fresh RNA ($r>=0.944$), when compared with QDR ($r>=0.929$) and AMB ($r>=0.810$). It was observed that AMB provided FFPERNA where miRNAs had the lowest correlation with fresh RNA, further validating the qRT-PCR results and indicating that this method of extraction appears to be the least suited for microRNA recovery from FFPE cells.

Figure 5:
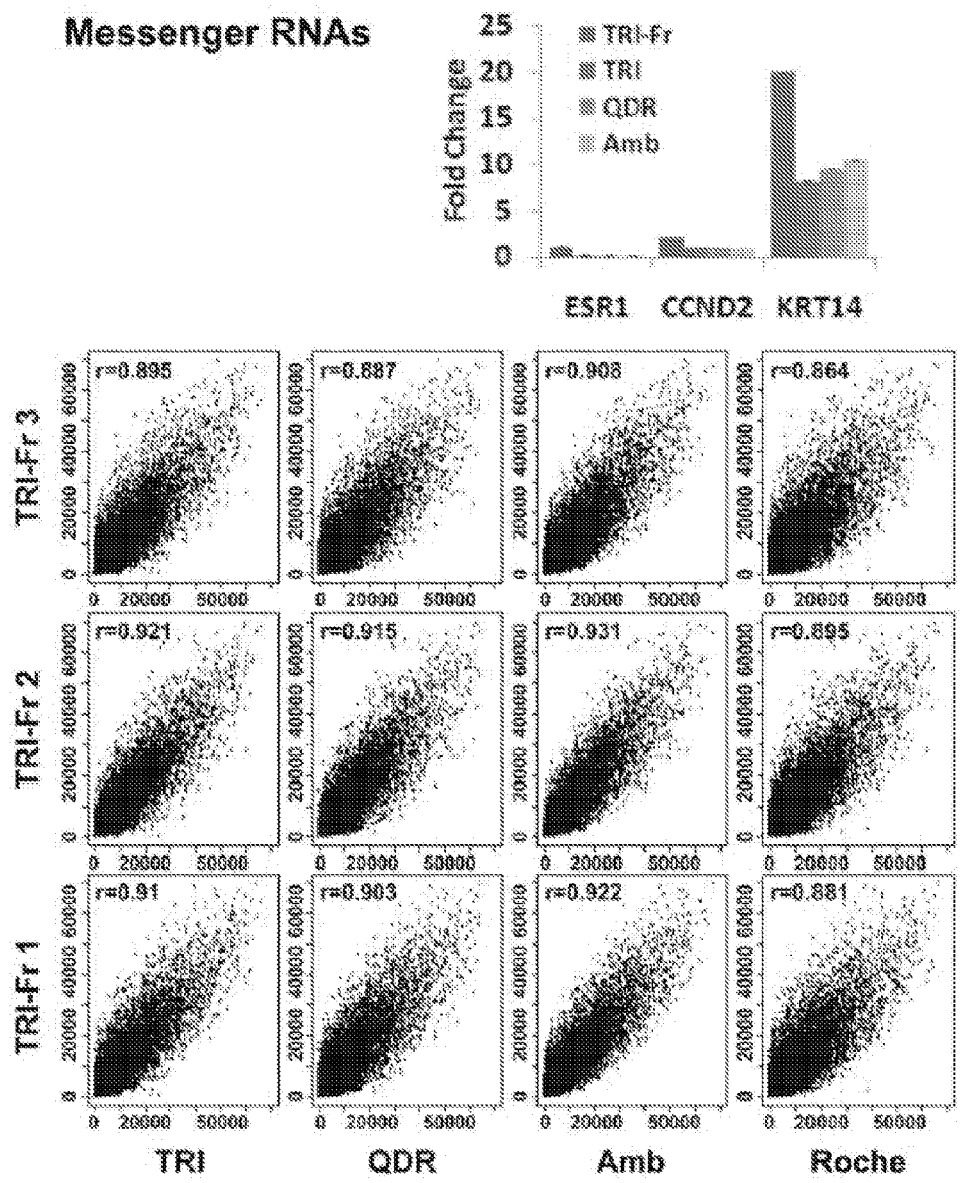
FIG. 5.

Gene Expression Analysis of Matched Fresh and FFPE RNA: Next, this study sought to determine if mRNA expression might be influenced by the FFPE-RNA extraction method and compared matched fresh and FFPE-RNA recovered by TRI, QDR, and AMB. First, this study performed qRT-PCR experiments on three differentially expressed genes in fresh MCF10A cells, ESR1 for low (MCF10A cells are considered ER negative cells), CCND2 for intermediate, and KRT14 for high expression (FIG. 5, bar graph). The data show that Taqman® qRT-PCR primers detect a significant decrease in expression in FFPE-RNA (FIG. 5, bar graph see three shades of blue), when compared to matched fresh RNA (FIG. 5, bar graph see dark blue). Next, the Illumina whole-genome cDNA-mediated Annealing, Selection, Extension and Ligation (WG-DASL) assay was used for high-throughput expression profiling of 24,526 genes to compare matched fresh and FFPERNA. Following Illumina's instructions for analysis of FFPE-RNA with the WG-DASL assay, this study used FFPE-RNA recovered with the high-pure RNA paraffin kit from Roche (FIG. 5, microarray data panels Roche). Based on gene expression analyses, there was a high correlation between matched fresh and FFPE-RNA ($r>=0.881$), with greater correlation using FFPE-RNA obtained with AMB ($r>=0.908$) and TRI ($r>=0.895$). Primers used for the WG-DASL assay span 50 nucleotides, whereas primers used to quantify ESR1, CCND2 and KRT14 spanned 62, 64 and 69 nucleotides, respectively, which might account for the decrease in expression measured in FFPE-RNA, when compared with fresh RNA.

Figures 6A, 6B:
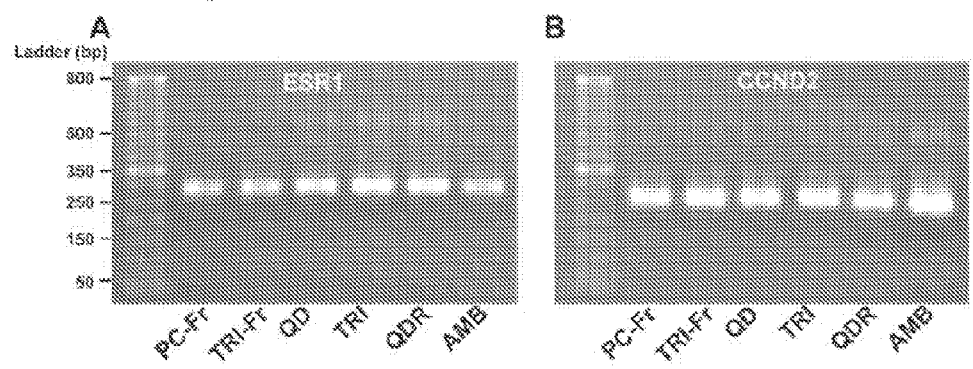
FIGS. 6A-6F.
Figure 6C:
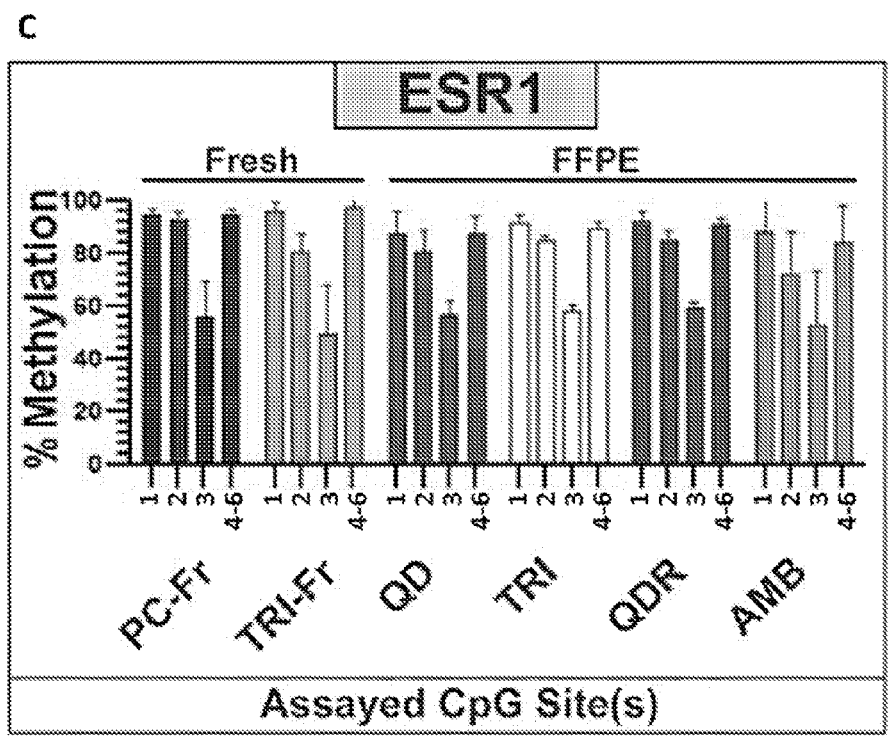
Figure 6D:
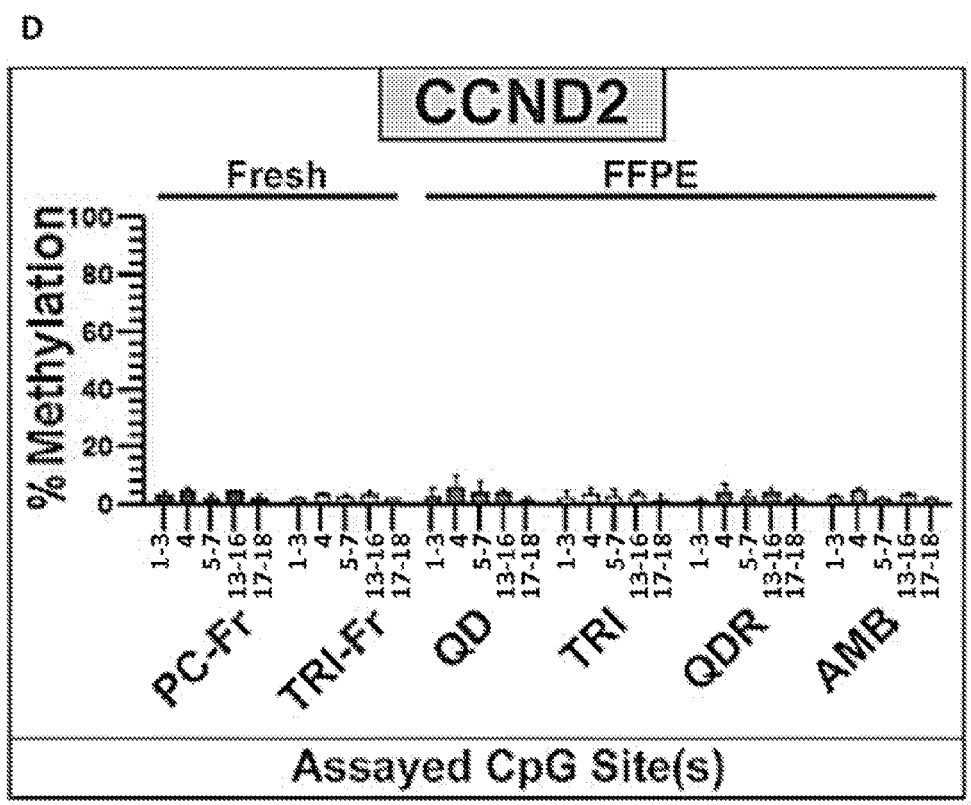
Figure 6E:
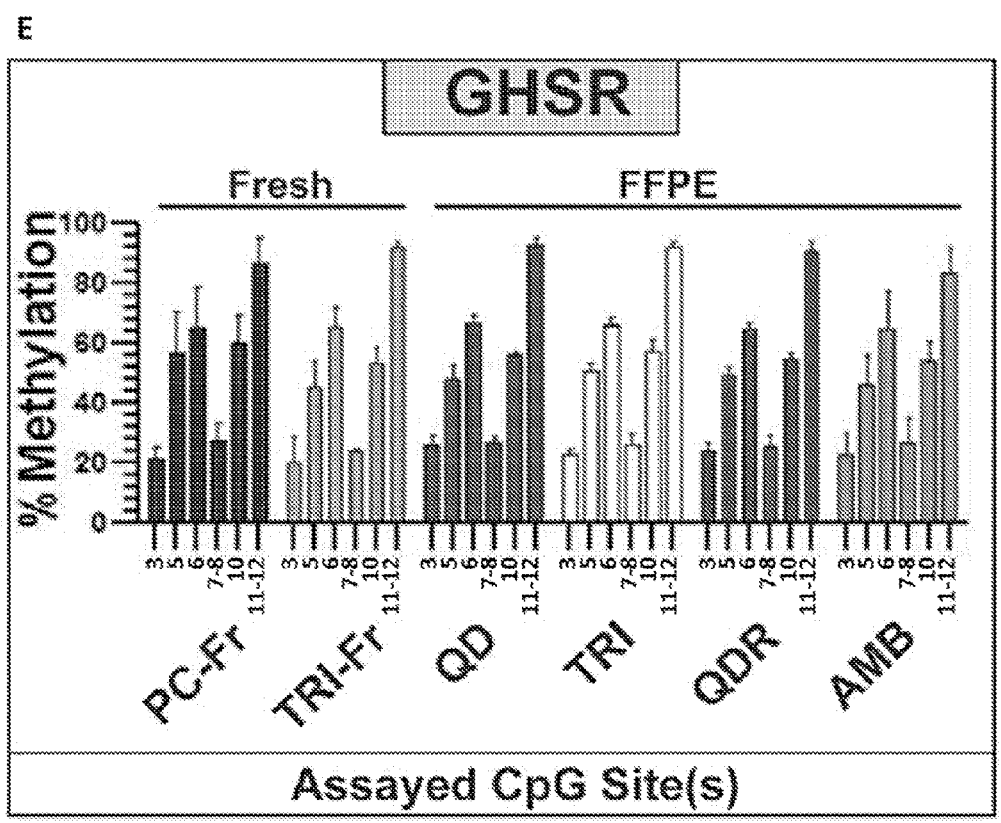
Figure 6F:
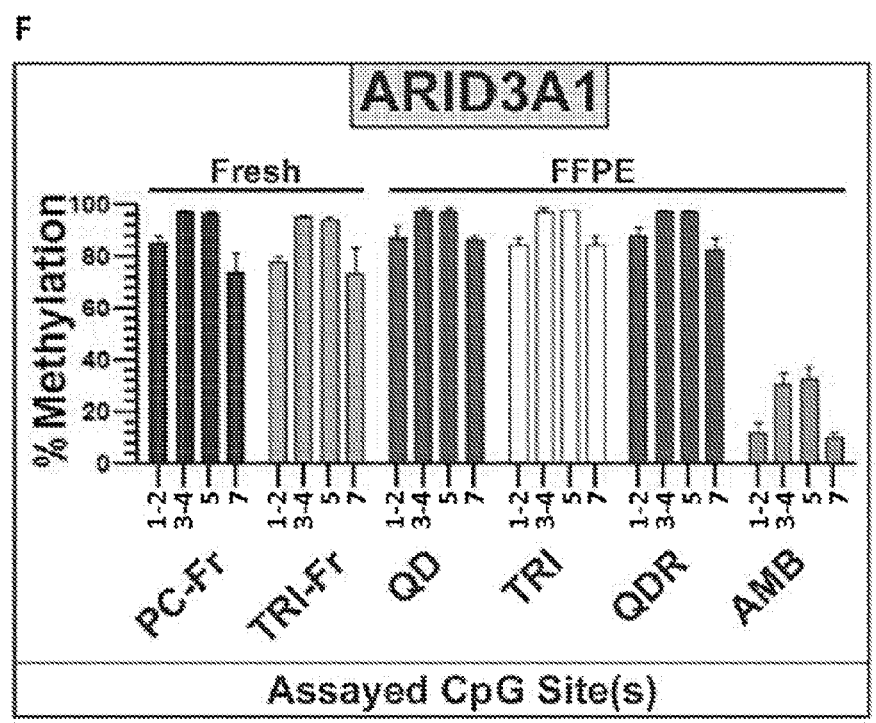

Methylation Analysis of Genomic DNA from Matched Fresh and FFPE DNA: Finally, single methylation assays were performed to assess the quality of genomic FFPE-DNA, by comparing it to matched fresh genomic DNA. The optimized approach combines PCR, a nucleotide sensitive reaction (FIG. 6A-B, ESR1 and CCND2), and mass spectrometry (MassARRAY EpiTYPER), a state-of-the-art analytical technology for measuring atomic mass differences (FIG. 6C-F). Using bisulfite-converted DNA from matched fresh and FFPE cells, this study quantified methylated CpG islands in the promoter regions of ESR1 and GHSR, in intron 1 of CCND2, and in intron 3 of ARID3A1 (FIG. 6C-F), identified using the MassArray Statistical package [27]. The results show that the methylation patterns of the regions analyzed for ESR1 and CCND2 correlate with the qRT-PCR data measured in FIG. 5 (high expression/low methylation and low expression/high methylation near). The results also show that methylation patterns observed in fresh DNA, purified by phenol-chloroform (FIG. 6C-F, PC-Fr) and by TRIzol (FIG. 6C-F, TRI-Fr), are well reproducible in FFPE-DNA obtained with the different approaches (FIG. 6C-F, QD, TRI, QDR, AMB). The PCR products obtained for the CpG islands tested for ESR1 and CCND2 were of comparable sizes between matched fresh and FFPE-DNAs (FIG. 6A-B) providing identical methylation patterns between fresh and FFPE-DNAs for each gene and for each extraction approach (FIG. 6C-D). GHSR and ARID3A1, two genes non-expressed in MCF10A cells (FIG. 6E-F), were also tested, and only observed methylation differences with AMB, with a 60-80% decrease for ARID3A1. The results show that only AMB provides FFPE-DNA that displays high variability in methylation patterns of the CpG islands measured.

Discussion

This study developed a chaotropic reagent-containing solution based approach (for example, employing TRIzol®-based (Invitrogen, CA, USA)) for co-extraction of genomic DNA and total RNA from archived specimens within a single reaction [11]. The approach allows maximal co-extraction of both nucleic acids without having to split the proteinase-K digested FFPE tissue prior to nucleic acid recovery or having to use additional FFPE tissue to obtain sufficient amounts of nucleic acid material. When compared to two commercial kits (Qiagen All-prep DNA/RNA FFPE kit and Ambion RecoverAll™ Total Nucleic acid isolation kit), in the context of matched fresh and FFPE MCF10A breast cells, the approach provided higher FFPE-DNA and FFPE-RNA yields as well as higher quality material for throughput analyses of mRNA, miRNA, and methylation analysis of genomic DNA.

For FFPE-RNA recovery, it was shown that the novel extraction method (TRI) is superior to the two commercial kits (QDR, AMB). Considering that RNA is highly degradable in solution and that some studies suggested that mildly degraded FFPE-RNA could still be subjected to linear amplification and conventional microarray analyses [12], FFPE-RNA extraction methods, based on proteinase-K (pK) digestion, have been extensively shortened (15 minutes at 56° C. for QDR, 15 minutes at 50 uC for AMB, compared to 45 minutes at 59° C. for TRI) to improve RNA quality. In particular the AMB, which in its earlier version suggested a 2-3 h digest at 55° C. [33] has been shortened to a 15 minutes digest at 55° C., a modification that might affect FFPERNA yields. Considering that the whole-genome cDNA mediated selection extension ligation (WG-DASL) assay, from Illumina, is designed to interrogate 50 nucleotide regions by RT and PCR [10,26,33], and massively-parallel sequencing technologies is designed for the analysis of short RNA sequences (reads<100 bps) [13], and in light of recent studies demonstrating that longer pK digestion provide larger amounts of FFPE-RNA and better analytical data [34,35], the need for short pK digestion and recovery of high quality RNA has decreased. In fact, using the WG-DASL, the mRNA expression profiling data shows the high correlation between matched fresh and FFPE-RNA obtained by all methods regardless of pK digest durations, with AMB providing the highest correlation (r>=0.908). However, for miRNA expression analysis, it was observed that AMB provided the lowest correlation ratios (r>=0.810), between fresh and FFPE-RNA, when compared to the QDR (r>=0.929) and TRI (r>=0.944), suggesting that different FFPE-RNA extraction methods can quantitatively and qualitatively affect the analysis of miRNAs. However, analyses reveal that co-extraction of DNA and RNA does not affect miRNA expression profiling results demonstrating that this approach provides high quality mRNA and miRNAs for molecular analyses.

For extraction of FFPE-DNA, the Qiagen QiaAmp FFPE DNA kit (QD; Qiagen, CA, USA) was used as a control for yield and quality, because it has been shown to be a robust approach when compared to other methods and kits [36] and the recovered FFPEDNA has successfully been used for genotyping studies [37], array CGH [38], genome-wide massively-parallel sequencing [13], and methylation studies [39]. The results show that QD provides larger amounts of FFPE-DNA than co-extraction (TRI, QDR) or separate extraction (AMB) methods. Based on analyses of freshly fixed specimens (1 month-old FFPE MCF10A), however, both co-extraction methods (TRI, QDR) still provide high DNA yields when compared to QD (80-90% of FFPE-DNA recovered by QD). When testing older archived specimens, which provide genomic DNA of lower quality (FIG. 9), analysis revealed that TRI performed better than QDR. These experiments suggest that while being time consuming (45 min pK for RNA, 48 hours pK digest, and use of the QD kit for DNA extraction) TRI is an efficient co-extraction approach for recovery of genomic DNA from older archived specimens. For analysis of the FFPE-DNA from 1 month-old archived MCF10 cells, bisulfite conversion and PCR reactions were used to assay hypo- and hyper-methylated CpG islands of FFPE genomic DNA. Analyses of four different CpG islands for four different genes suggests that TRI and QDR provide higher quality FFPE-DNA than AMB, which yielded material that displayed higher variation in methylation levels. TRI, which incorporates the use of the QD kit for FFPE-DNA purification, and QDR include a heat-treatment step at 90° C. to increase FFPE-DNA quality through removal of FFPE-DNA/protein cross-links [20-23]. This heat-treatment step, which is not described in the procedure of AMB, might account for the discrepancies, between matched fresh and FFPE-DNA, observed in the methylation analysis data. It is important to note that when using older FFPE specimens, which yield lower quality genomic DNA, methylation analyses should be performed on CpG islands spanning less than 300 by for consistent results (FIG. 9)

The analyses demonstrated that the two co-extraction methods tested (optimized TRIzol® method (TRI), and Qiagen AllPrep DNA/RNA FFPE kit (QDR)) provided higher yields as well as more reliable material for molecular studies than the separate extraction method (Ambion RecoverAll™ kit (AMB)). However, advantages and disadvantages of either method should be weighted carefully. On one side, the QDR has a short pK digestion (15 minutes), and might be automated, but it might not provide the highest amounts of FFPE DNA and RNA. On the other side the optimized method (TRI) in one embodiment employs two digests (45 min and 48 h), use the QD kit for final purification, and is incompatible with automation (due to the use of TRIzol®), but the results indicate that it provides higher genomic DNA yields when used with older archived specimens (FIG. 9) and generally higher RNA yields than QDR. For large-scale studies, automation might be important, and thus the method described by Hennig et al. [2010], in which nucleic acids released by proteinase K digestion are magnetically purified, split, and subjected to RNAse for DNA purification and DNAse for RNA purification, might be more appropriate [40]. However, the results demonstrate that while the use of nucleases (RNAse or DNAse) assures higher DNA or RNA quality, dividing the pK-digested tissue solution in smaller fractions significantly decreases the amount of DNA and RNA recoverable from a single sample and thus represents a limiting approach for correlative studies or storage of optimal amounts of material for future studies. It is important to note that several other commercial kits commercialized for FFPE-DNA and FFPE-RNA recovery only allow separate extraction by splitting the pk-digested solution and include: the Norgen FFPE RNA/DNA kit (Norgen Biotek, Canada); the AxyPrep Mag FFPE (DNA/RNA/miRNA) kit (Axygen Biosciences, CA, USA); and the Aline® FFPE Magapure kit (Aline Bioscience, MA, USA).

In conclusion, this study is the first to demonstrate that high quality FFPE-DNA can be purified from the lower aqueous phase of TRIzol, without affecting optimal recovery of FFPE-RNA from the upper organic phase. It was demonstrated that co-extraction of DNA and RNA from a single archived specimen is highly efficient and provides the options of direct usage or storage of material for additional or subsequent studies. Based on the experiments, researchers should extract genomic DNA and total RNA at the same time for effective use of archived specimens.

REFERENCES

1. Klopfleisch R, Weiss A T, Gruber A D (2011) Excavation of a buried treasure—DNA, mRNA, miRNA and protein analysis in formalin fixed, paraffin embedded tissues. Histol Histopathol 26: 797-810.
2. Ren Z P, Sallstrom J, Sundstrom C, Nister M, Olsson Y (2000) Recovering DNA and optimizing PCR conditions from microdissected formalin-fixed and paraffin-embedded materials. Pathobiology 68: 215-217.
3. Lehmann U, Kreipe H (2001) Real-time PCR analysis of DNA and RNA extracted from formalin-fixed and paraffin-embedded biopsies. Methods 25: 409-418.
4. Johnson N A, Hamoudi R A, Ichimura K, Liu L, Pearson D M, et al. (2006) Application of array CGH on archival formalin-fixed paraffin-embedded tissues including small numbers of microdissected cells. Lab Invest 86: 968-978.
5. Schweiger M R, Kerick M, Timmermann B, Albrecht M W, Borodina T, et al. (2009) Genome-wide massively parallel sequencing of formaldehyde fixed paraffin embedded (FFPE) tumor tissues for copy-number- and mutation analysis. PLoS One 4: e5548.
6. Dallol A, Al-Ali W, Al-Shaibani A, Al-Mulla F (2011) Analysis of DNA methylation in FFPE tissues using the MethyLight technology. Methods Mol Biol 724: 191-204.
7. Gagnon J F, Sanschagrin F, Jacob S, Tremblay A A, Provencher L, et al. (2010) Quantitative DNA methylation analysis of laser capture microdissected formalin-fixed and paraffin-embedded tissues. Exp Mol Pathol 88: 184-189.
8. Thirlwell C, Eymard M, Feber A, Teschendorff A, Pearce K, et al. (2010) Genome-wide DNA methylation analysis of archival formalin-fixed paraffin embedded tissue using the Illumina Infinium HumanMethylation27 Bead Chip. Methods 52: 248-254.
9. Farragher S M, Tanney A, Kennedy R D, Paul Harkin D (2008) RNA expression analysis from formalin fixed paraffin embedded tissues. Histochem Cell Biol 130: 435-445.
10. April C, Klotzle B, Royce T, Wickham-Garcia E, Boyaniwsky T, et al. (2009) Whole-genome gene expression profiling of formalin-fixed, paraffin-embedded tissue samples. PLoS One 4: e8162.
11. Loudig O, Milova E, Brandwein-Gensler M, Massimi A, Belbin T J, et al. (2007) Molecular restoration of archived transcriptional profiles by complementarytemplate reverse-transcription (CT-RT). Nucleic Acids Res 35: e94.
12. Penland S K, Keku T O, Torrice C, He X, Krishnamurthy J, et al. (2007) RNA expression analysis of formalin-fixed paraffin-embedded tumors. Lab Invest 87: 383-391.
13. Qu K, Morlan J, Stephans J, Li X, Baker J, et al. (2010) Transcriptome profiling from formalin-fixed, paraffin-embedded tumor specimens by RNA-seq. Genome Biololgy 11 Suppl 1: p 31.
14. Weng L, Wu X, Gao H, Mu B, Li X, et al. (2010) MicroRNA profiling of clear cell renal cell carcinoma by whole-genome small RNA deep sequencing of paired frozen and formalin-fixed, paraffin-embedded tissue specimens. J Pathol 222: 41-51.
15. Streichert T, Otto B, Lehmann U (2011) microRNA Expression Profiling in Archival Tissue Specimens: Methods and Data Processing. Mol Biotechnol.
16. Giricz O, Reynolds P A, Ramnauth A, Liu C, Wang T, et al. (2011) Hsa-miR-375 is differentially expressed during breast lobular neoplasia and promotes loss of mammary acinar polarity. J Pathol.
17. Bonin S, Hlubek F, Benhattar J, Denkert C, Dietel M, et al. (2010) Multicentre validation study of nucleic acids extraction from FFPE tissues. Virchows Arch 457: 309-317.
18. Okello J B, Zurek J, Devault A M, Kuch M, Okwi A L, et al. (2010) Comparison of methods in the recovery of nucleic acids from archival formalin-fixed paraffin embedded autopsy tissues. Anal Biochem 400: 110-117.
19. Chaw Y F, Crane L E, Lange P, Shapiro R (1980) Isolation and identification of cross-links from formaldehyde-treated nucleic acids. Biochemistry 19: 5525-5531.
20. Jackson V (1978) Studies on histone organization in the nucleosome using formaldehyde as a reversible cross-linking agent. Cell 15: 945-954.
21. Shi S R, Datar R, Liu C, Wu L, Zhang Z, et al. (2004) DNA extraction from archival formalin-fixed, paraffin-embedded tissues: heat-induced retrieval in alkaline solution. Histochem Cell Biol 122: 211-218.
22. Wu L, Patten N, Yamashiro C T, Chui B (2002) Extraction and amplification of DNA from formalin-fixed, paraffin-embedded tissues. Appl Immunohistochem Mol Morphol 10: 269-274.
23. Hamatani K, Eguchi H, Takahashi K, Koyama K, Mukai M, et al. (2006) Improved RT-PCR amplification for molecular analyses with long-term preserved formalin-fixed, paraffin-embedded tissue specimens. J Histochem Cytochem 54: 773-780.
24. Masuda N, Ohnishi T, Kawamoto S, Monden M, Okubo K (1999) Analysis of chemical modification of RNA from formalin-fixed samples and optimization of molecular biology applications for such samples. Nucleic Acids Res 27: 4436-4443.
25. Triant D A, Whitehead A (2009) Simultaneous extraction of high-quality RNA and DNA from small tissue samples. J Hered 100: 246-50.
26. Huang W Y, Sheehy T M, Moore L E, Hsing A W, Purdue M P (2010) Simultaneous recovery of DNA and RNA from formalin-fixed paraffin embedded tissue and application in epidemiologic studies. Cancer Epidemiol Biomarkers Prey 19: 973-977.
27. Loudig O, Brandwein-Gensler M, Kim R S, Lin J, Isayeva T, et al. (2011) Illumina whole-genome complementary DNA-mediated annealing, selection, extension and ligation platform: assessing its performance in formalin-fixed, paraffin-embedded samples and identifying invasion pattern-related genes in oral squamous cell carcinoma. Hum Pathol.
28. Thompson R F, Suzuki M, Lau K W, Greally J M (2009) A pipeline for the quantitative analysis of CG dinucleotide methylation using mass spectrometry. Bioinformatics 25: 2164-2170.
29. Li L C, Dahiya R (2002) MethPrimer: designing primers for methylation PCRs. Bioinformatics 18: 1427-1431.
30. Aranyi T, Tusnady G E (2007) BiSearch: ePCR tool for native or bisulfite-treated genomic template. Methods Mol Biol 402: 385-402.
31. Karolchik D, Hinrichs A S, Kent W J (2011) The UCSC Genome Browser. Curr Protoc Hum Genet Chapter 18: Unit 18 16.
32. Bolstad B M, Irizarry R A, Astrand M, Speed T P (2003) A comparison of normalization methods for high density oligonucleotide array data based on variance and bias. Bioinformatics 19: 185-193.
33. Liu A, Xu X (2011) MicroRNA isolation from formalin-fixed, paraffin embedded tissues. Methods Mol Biol 724: 259-267.
34. Abramovitz M, Ordanic-Kodani M, Wang Y, Li Z, Catzavelos C, et al. (2008) Optimization of RNA extraction from FFPE tissues for expression profiling in the DASL assay. Biotechniques 44: 417-423.
35. Glenn S T, Head K L, Teh B T, Gross K W, Kim H L (2010) Maximizing RNA yield from archival renal tumors and optimizing gene expression analysis. J Biomol Screen 15: 80-85.
36. Munoz-Cadavid C, Rudd S, Zaki S R, Patel M, Moser S A, et al. (2010) Improving molecular detection of fungal DNA in formalin-fixed paraffin embedded tissues: comparison of five tissue DNA extraction methods using panfungal PCR. J Clin Microbiol 48: 2147-2153.
37. Cannon-Albright L A, Cooper K G, Georgelas A, Bernard P S (2011) High quality and quantity Genome-wide germline genotypes from FFPE normal tissue. BMC Res Notes 4: 159.
38. Ghazani A A, Arneson N C, Warren K, Done S J (2006) Limited tissue fixation times and whole genomic amplification do not impact array CGH profiles. J Clin Pathol 59: 311-315.
39. Stanzer S, Balic M, Strutz J, Heitzer E, Obermair F, et al. (2010) Rapid and reliable detection of LINE-1 hypomethylation using high-resolution melting analysis. Clin Biochem 43: 1443-1448.
40. Henning G, Gehrmann M, Stropp U, Brauch H, Fritz P, Eichelbaum M, Schwab M, Schroth W (2010) Automated extraction of DNA and RNA from a single formalin-fixed paraffin-embedded tissue section for analysis of both single nucleotide polymorphisms and mRNA expression. Clin Chem 56: 1845-53.

What is claimed is:
1. A method of recovering both RNA and DNA from a biological sample comprising contacting the sample with a monophasic solution comprising phenol and guanidine isothiocyanate,
obtaining RNA from the resultant upper phase,
contacting the resultant lower phase with an amount of ethanol and centrifuging for a time sufficient to create a pellet,
contacting the pellet with an amount of a first buffer solution and proteinase K, purifying DNA from the pellet by contacting with an amount of a second buffer and an amount of ethanol, binding, washing and eluting the purified DNA so as to obtain the DNA, thereby recovering both RNA and DNA from the same biological sample.

2. The method of claim 1, wherein the monophasic solution also comprises ammonium thiocyanate.

3. The method of claim 1, wherein the phenol is 30-60% of the monophasic solution and the guanidine isothiocyanate is 15-40% of the monophasic solution.

4. The method of claim 1, wherein the monophasic solution comprises ammonium thiocyanate at 7-13% of the solution.

5. The method of claim 1, wherein the biological sample comprises a formalin-fixed and paraffin-embedded biological sample.

6. The method of claim 1, wherein the biological sample comprises serum, plasma, blood, urine, tears, saliva, or semen.

7. The method of claim 1, wherein the biological sample comprises a purified exosome.

8. The method of claim 1, wherein obtaining RNA from the resultant upper phase comprises contacting the upper phase with isopropanol, sodium acetate and linear acrylamide then centrifuging with ethanol a sufficient amount of times to obtain a pellet, air drying the pellet, contacting with buffer and centrifuging a further amount of time so as to obtain the RNA.

9. The method of claim 1, wherein the biological sample is formalin-fixed.

10. The method of claim 1, wherein the biological sample is paraffin-embedded.

11. The method of claim 1, further comprising, after contacting the resultant lower phase with an amount of ethanol and centrifuging at a temperature below 10° C. for a time sufficient to create a pellet, air drying the pellet and centrifuging it again in an amount of 80% ethanol and then air-drying the pellet, prior to contacting the pellet with an amount of a first buffer solution and proteinase K.

12. The method of claim 1, wherein the pellet is contacted with the first buffer solution and proteinase K for at least a 20 hour period, and then washed and contacted with a second amount of a first buffer solution and proteinase K for at least a second 20 hour period.

13. The method of claim 1, wherein the pellet is contacted with the first buffer solution and proteinase K for at least a 24 hour period, and then washed and contacted with a second amount of a first buffer solution and proteinase K for at least a second 24 hour period.

14. The method of claim 1, wherein the sample comprises genomic DNA.

15. The method of claim 1, wherein the sample comprises microRNA.

16. The method of claim 1, further comprising digesting the biological sample prior to contacting it with the monophasic solution.

17. The method of claim 1, wherein the contacting the pellet with an amount of a first buffer solution and proteinase K is performed for a time sufficient to effect digestion of the majority of cross-linked proteins in the pellet.

18. The method of claim 1, wherein, in contacting the resultant lower phase with an amount of ethanol, the centrifuging occurs at a temperature below 10° C. for a time sufficient to create a pellet.

19. A kit for performing the method of claim 1 comprising
an amount of powdered Proteinase K;
an amount of a chaotropic reagent for separation of RNA and DNA fractions;
one or more binding columns to recover the DNA;
optionally, if the RNA is not to be precipitated, a binding column to recover the RNA;
optionally, if the RNA is to be precipitated, an amount of linear acrylamide for performing precipitation of RNA;
one or more binding buffers for the binding columns;
one or more wash buffers for the binding columns;
RNAse/DNase-free water for elution of DNA from binding columns;
and instructions for use.

* * * * *